(12) United States Patent
Culbertson et al.

(10) Patent No.: US 6,783,647 B2
(45) Date of Patent: Aug. 31, 2004

(54) MICROFLUIDIC SYSTEMS AND METHODS OF TRANSPORT AND LYSIS OF CELLS AND ANALYSIS OF CELL LYSATE

(75) Inventors: Christopher T. Culbertson, Oak Ridge, TN (US); Stephen C. Jacobson, Knoxville, TN (US); Maxine A. McClain, Knoxville, TN (US); J. Michael Ramsey, Knoxville, TN (US)

(73) Assignee: UT-Battelle, LLC, Oak Ridge, TN (US)

(*) Notice: Subject to any disclaimer, the term of this patent is extended or adjusted under 35 U.S.C. 154(b) by 88 days.

(21) Appl. No.: 10/041,821

(22) Filed: Oct. 19, 2001

(65) Prior Publication Data

US 2003/0075446 A1 Apr. 24, 2003

(51) Int. Cl.[7] ..................... G01N 27/447; G01N 27/453
(52) U.S. Cl. ....................... 204/453; 204/451; 204/602; 204/601; 204/604
(58) Field of Search ................................. 204/453, 602, 204/604, 450, 451, 600, 601; 435/173.7, 259, 306.1

(56) References Cited

U.S. PATENT DOCUMENTS

| | | |
|---|---|---|
| 4,676,274 A | 6/1987 | Brown |
| 5,304,487 A | 4/1994 | Wilding et al. |
| 5,858,187 A | 1/1999 | Ramsey et al. |
| 5,858,195 A | 1/1999 | Ramsey |
| 6,001,229 A | 12/1999 | Ramsey |
| 6,033,546 A | 3/2000 | Ramsey |
| 6,043,066 A | 3/2000 | Mangano et al. |
| 6,071,394 A | 6/2000 | Cheng et al. |
| 6,110,343 A | 8/2000 | Ramsey et al. |
| 6,120,666 A | 9/2000 | Jacobson et al. |
| 6,231,737 B1 | 5/2001 | Ramsey et al. |
| 6,287,831 B1 | 9/2001 | Tai et al. |
| 6,322,683 B1 * | 11/2001 | Wolk et al. ............... 204/600 |
| 6,544,734 B1 * | 4/2003 | Briscoe et al. ............. 435/6 |
| 6,572,830 B1 * | 6/2003 | Burdon et al. ......... 422/186.29 |

FOREIGN PATENT DOCUMENTS

| | | | | |
|---|---|---|---|---|
| GB | 2355717 A | * | 5/2001 | ........... C12N/15/10 |
| WO | 9925816 A1 | * | 5/1999 | ........... C12N/13/00 |
| WO | 9938612 A1 | * | 8/1999 | ........... B01J/19/00 |

OTHER PUBLICATIONS

Sale, A.J.H. et al. "Effects of High Electric Fields on Micro–Organisms III. Lysis of Erythrocytes and Protoplasts"; Biochim. Biophyso Acta, 163: 37–43 (1968).

(List continued on next page.)

*Primary Examiner*—Alex Noguerola
(74) *Attorney, Agent, or Firm*—Dann, Dorfman, Herrell & Skillman, P.C.

(57) ABSTRACT

Microfluidic systems and methods are disclosed which are adapted to transport and lyse cellular components of a test sample for analysis. The disclosed microfluidic systems and methods, which employ an electric field to rupture the cell membrane, cause unusually rapid lysis, thereby minimizing continued cellular activity and resulting in greater accuracy of analysis of cell processes.

43 Claims, 8 Drawing Sheets

OTHER PUBLICATIONS

Kinosita, Jr. K. et al. "Voltage–Induced Pore Formation and Hemolysis of Human Erythrocytes"; Biochim. Biophys. Acta, 471: 227–242 (1977).

Kinosita, K. et al. "Hemolysis of Human Erythrocytes by a Transient Electric Field"; Proceedings of the National Academy of Sciences of the United States of America, 74(5): 1923–1927 (1977).

Li, P.C.H. et al. "Transport, Manipulation, and Reaction of Biological Cells On–Chip Using Electrokinetic Effects"; Anal. Chem., 69: 1564–1568 (Apr. 15, 1997).

Chen, S. et al. "Continuous Cell Introduction for the Analysis of Individual Cells by Capillary Electrophoresis"; Anal. Chem. 73: 111–118 (Jan. 1, 2001).

Soughayer, J.S. et al. "Characterization of Cellular Optoporation with Distance"; Anal. Chem., 72: 1342–1347 (Mar. 15, 2000).

McKnight, T.E. et al. "Electroosmotically Induced Hydraulic Pumping with Integrated Electrodes on Microfluidic Devices"; Anal. Chem., 73: 4045–4049 (Aug.15, 2001).

Duffy, D.C. et al. "Rapid Prototyping of Microfluidic Systems in Poly(dimethylsiloxane)"; Anal. Chem., 70: 4974–4984 (Dec. 1,1998).

* cited by examiner

MICROFLUIDIC SYSTEMS AND METHODS OF TRANSPORT AND LYSIS OF CELLS AND ANALYSIS OF CELL LYSATE This invention was made with Government support under contract DE-AC05-00OR22725 awarded by the United States Department of Energy to UT-Battelle, LLC. The Government has certain rights in this invention.

FIELD OF THE INVENTION

This invention relates to molecular biology, and in particular, to the use of an applied electric field in a microfluidic system for the manipulation of biological samples comprising cells and cell lysate(s) for subsequent analysis.

BACKGROUND OF THE INVENTION

Interest in microfabricated devices for chemical sensing and analysis has grown substantially over the past decade, primarily because these miniature devices have the potential to provide information rapidly and reliably at low cost. Microchips fabricated on planar substrates are advantageous for manipulating small sample volumes, rapidly processing materials, and integrating sample pretreatment and separation strategies. The ease with which materials can be manipulated and the ability to fabricate structures with interconnecting channels that have essentially no dead volume contribute to the high performance of these devices. See, for example U.S. Pat. Nos. 5,858,195 and 6,001,229, which are commonly owned with this application. To carry out a complete analysis, many different kinds of functional elements can be designed and integrated on microchips. These elements include filters, valves, pumps, mixers, reactors, separators, cytometers and detectors, which can be operatively coupled together under computer control to enable the implementation of a wide range of microchip-based analyses.

One area of particular interest is the analysis of cells and cell populations. At present most techniques for cellular analysis depend upon pooling a population of cells to obtain a large enough quantity of analyte for detection. Pooling of cells, however, obscures any variation in analyte concentration from cell to cell. For many studies average analyte values across a large population of cells will be acceptable; however, for the study of processes such as carcinogenesis, the ability to quantitate analytes in individual cells is required so that rare mutations in cells, which lead to drastic changes in cell metabolism and progression to cancer, can be detected.

With the advances in Capillary Electrophoresis over the last two decades the quantitation of analytes in individual cells has become feasible albeit slow because of the intensive manual manipulations which have to be performed. The potential to automate and integrate cell transport, manipulation and lysis with separation and analyte detection make microfluidic devices a desirable platform for performing high throughput screening of individual cells from large populations. A key step in integrating cell handling with analyte detection and quantitation is providing a method of cell lysis which is rapid and generates small axial extent plugs for subsequent analysis. Because the resolution or separation between any pair of compounds can be detrimentally affected by long injection plug lengths, small axial extent plugs are important for a successful separation. It should be noted, however, that while small axial extent plugs are desired, the contents of the cell after lysis should be spread over several cell volumes so that reaction pathways within the cell are terminated and proteolytic enzymes released from vesicles during lysis are sufficiently diluted. This will prevent the possible digestion of proteins of interest.

The use of an applied electric field for cell lysis is known. For example, the lysis of erythrocytes in suspension by pulsed electric fields has been reported both for bovine (Sale and Hamilton, "Effects of High Electric Fields on Microorganisms III, Lysis of Erythrocytes and Protoplasts", *Biochim et Biophys Acta,* 163:37 (1967)) and human erythrocytes (Kinosita and Tsong, "Voltage-Induced Pore Formation and Hemolysis of Human Erythrocytes", *Biochim et Biophys Acta,* 471:227 (1977); and Kinosita and Tsong, "Hemolysis of Human Erythrocytes by a Transient Electric Filed", *Proc Nail Acad Sci.,* 74:1923 (1977)). These reports indicate that applied electric fields resulting in cellular transmembrane potentials on the order of 1 Volt can result in lysis of erythrocytes. However, these previously reported cell lysis techniques utilizing an electric field are typically carried out in a macroscale device, rather than a microchip device. Consequently, such techniques are lacking in certain respects. Specifically, the conditions employed in macroscale electric cell lysis devices do not consistently release relatively high molecular weight nucleic acid molecules, because such molecules do not readily pass through the pores created in the cell membrane by this lysis technique. Also, the existing macroscale, electric lysis devices function as stand-alone units, thus precluding integration of cell manipulation and lysis with separation and analysis of cell lysate in a unitary device.

Other methods of cell manipulation and/or lysis on microscale devices have been proposed. See, for example, U.S. Pat. Nos. 4,676,274 and 5,304,487. Chemical lysis on a microchip device has been demonstrated by mixing a surfactant, i.e. sodium dodecylsulfate, with canine erythrocyte cells. (Li and Harrison, Anal. Chem., 69:1564–1568 (1997)). This report indicates that the cells were lysed in under 0.3 sec. No subsequent analysis of the cellular contents, however, was reported. Single erythrocytes have been lysed and the cell contents separated using two capillaries across which an electric field is applied. A gap of about 5 $\mu$m is provided between the two capillaries. As intact cells pass through the gap, they are lysed and the contents of the lysed cells are transported to the second capillary for separation. The lysis is presumed to be caused by the mechanical shear stresses induced by the change in electric field strength between the capillaries and the gap region. The gap region is considerably larger in cross sectional area, so that the field strength and, therefore, cell velocity is lower than in the capillaries. See, Chen and Lillard, Anal. Chem., 73:111–18 (2001).

Cell lysis can be considered an extreme form of cell membrane permeablization (poration). Optoporation has been carried out using highly focused light from a pulsed laser (Soughhayer et al., Anal. Chem. 72(6): 1342–1347 (2000)). The laser is focused near the cell at the aqueous/glass interface. When the laser is pulsed, a stress (shock) wave is generated which transiently permeablizes the cell. This technique has been shown to be capable of lysing cells, as well. The occurrence of cell lysis or poration only is a function of the cell's distance from the laser focal spot.

Although the above-mentioned cell lysis techniques of the prior art are useful for certain applications, there exists a need in the art for microchip-based cell manipulations and lysis which is sufficiently rapid to minimize continued cellular activity after lysis, thus producing greater accuracy in the analysis of cell processes.

SUMMARY OF THE INVENTION

In accordance with one aspect of the present invention, there is provided a method of releasing the intracellular contents of at least one cell of a cell-containing fluid sample for analysis. The method of the invention comprises providing a substrate having a microchannel structure which includes one or more microchannel(s). An electric field is generated from a source of electric potential and applied in a spatially defined region of the aforementioned microchannel, which functions as a cell lysis region. The strength of the applied electric field is adequate to induce cell lysis. At least one cell of the fluid sample is positioned in the cell lysis region for a time sufficient to release the intracellular contents into the fluid sample. The released intracellular contents form an analyte plug of narrow axial extent in the microchannel.

According to another aspect of the invention, there is provided a microfluidic system for transport and lysis of at least one cell of a cell-containing fluid sample. The microfluidic system of this embodiment of the invention comprises a source of electric potential and a solid substrate including one or more microchannel(s) with a longitudinal axis, and a cell lysis region between first and second electrical contacts positioned adjacent (i.e. on or in close proximity to) microchannel wall portions on different sides of the longitudinal axis. The electrical contacts, which are spatially separated by the cell lysis region and electrically isolated from one another, are connected to a source of electric potential, which is operative to apply an electric field to the cell lysis region, transverse to the fluid sample flow path, within the microchannel space between the electrical contacts. The system also includes means for transporting the cell-containing fluid sample along the aforementioned microchannel.

According to a further aspect of this invention, there is provided a microfluidic system for transport and lysis of at least one cell of a cell-containing fluid sample and separation of its intracellular content. This system comprises a solid substrate having one or more microchannel(s) disposed therein, which includes a cell transport segment and a separation segment with first and second end portions. A first and a second electrode are provided along the aforementioned microchannel, intermediate the transport segment and the separation segment, and are spatially separated from one another, defining a space in the microchannel between them that serves as a cell lysis region. The electrodes are connected to a source of electric potential to apply an electric field to the cell lysis region. This system further includes means for flowing the cell-containing fluid sample through the aforementioned microchannel and means for applying an electric potential difference between the first and second separation segment end portions for effecting separation of the intracellular contents of lysed cells.

The microfluidic system and methods of this invention enable examination of the contents of single cells with high throughput. Consequently, this invention is expected to have considerable utility for facilitating research in the life sciences, and especially the pharmaceutical industry. For example, implementation of this invention in the pharmaceutical industry could expedite screening of cellular responses to large combinatorial libraries of potential novel drugs. In addition, the present invention can be used to advantage for the study of carcinogenesis or oncogenesis by assisting in the detection of rare cell mutations at an early stage, which is considered essential to the successful treatment of various forms of cancer. This invention may also be used to further elucidate metabolic pathways in cells.

BRIEF DESCRIPTION OF THE DRAWINGS

In FIG. 1A, cell lysis is effected in the applied electric field generated between a first electrical contact integrated into the microchannel and a second electrical contact positioned at or near the microchannel terminus, e.g. in a reservoir. FIG. 1B shows a different microchannel structure, in which a bridging membrane is included to provide electrical contact between the vertical and horizontal channels, without creating significant concurrent fluid flow. FIGS. 1C–1E show microchannel structures which have, as a common feature, a pair of electrical contacts which generate an electric field, causing cell lysis in the microchannel space between the electrical contacts. The microchannel structure of FIG. 1C also includes a separate means for initiating a cell lysis electric field, recording a time mark to indicate the start of a separation process, or controlling fluid sample transport, such as starting and/or stopping sample flow.

FIG. 2A shows a microchannel structure with a single auxiliary or side channel forming a tee-shaped intersection with the transport/lysis microchannel. FIG. 2B shows a cross design including two (2) side channels intersecting the transport/lysis microchannel on opposite sides thereof. In the microchannel structure illustrated in FIGS. 2A and 2B, the cell is exposed to the electric field upon entering the intersection. FIG. 2C shows an alternative cross microchannel structure designed for injection of a dilution buffer into the transport/lysis microchannel in order to minimize localized heating of the fluid sample comprising physiological buffer, while allowing maintenance of a high electric field in the channel segment downstream of the intersection for cell lysis and subsequent separation.

FIG. 5A shows the basic microchannel structure with electrodes placed at the termini (e.g., in fluid reservoirs) of side channels that intersect the transport/lysis microchannel. The arrow indicates the direction of pressure driven flow of the fluid sample. FIG. 5B shows the cell being transported toward the intersection via the pressure driven flow. FIG. 5C illustrates lysis of the cell at the intersection and release of the intracellular content(s) which begin migrating along the right side channel. FIG. 5D shows chemical separation of the cell lysate along the right side channel.

DETAILED DESCRIPTION OF THE INVENTION

The microfluidic devices and systems described herein can be made using various microfabrication techniques, as described in the aforementioned U.S. Pat. Nos. 6,001,229, issued Dec. 14, 1999 and 6,033,546, issued Mar. 7, 2000, both to J. M. Ramsey, as well as in U.S. patent application Ser. No. 09/244,914, filed Feb. 4, 1999 in the names of S. C. Jacobson et al. The devices and systems of this invention may also include means to induce pressure electrokinetically, for effecting material transport, as described in U.S. Pat. Nos. 6,110,343 and 5,231,737 to R. Ramsey and J. M. Ramsey. The entire disclosures of the last mentioned patents and application are incorporated by reference in the present application.

In embodiments of the invention employing one or more reservoirs for delivery or collection of a test sample, diluent, reagent or the like, electrode placement in a reservoir is done in the manner described in the patents and patent application referred to immediately above. Integration of an electrode into a microchannel structure, which is a feature of certain embodiments of this invention, may be done by depositing a thin metal film (~100 nm) of either Ti or Cr as an adhesion layer on a glass substrate followed by a thin metal film of gold (~300 nm). Photoresist is then spun on the metallized substrate and a mask of the desired electrode pattern is placed on top of the photoresist covered metallized substrate. The areas of the photoresist exposed, i.e., not covered by the electrode pattern, are removed, and the metal etched away. See, e.g., McKnight et al., 2001. Anal. Chem 73, 4045–4049. This leaves the glass substrate with a finished electrode pattern, onto which a poly(dimethylsiloxane) (PDMS) substrate with channels molded therein can be bonded. The bonding can be accomplished by either simple contact bonding or through covalent bonding generated by exposing the glass and PDMS substrates to an oxygen plasma and then bringing them quickly into contact with each other. See, e.g., Duffy et al., 1998, Anal. Chem. 70, 4974. The entire disclosures of the last-mentioned two literature references are incorporated by reference in the present application. See also, the aforementioned U.S. patent application Ser. No. 09/244,914.

The microfluidic devices and systems used in practicing this invention can be made out of a variety of substrate materials, including glass, fused silica and various polymeric materials, such as PDMS or combinations of such materials, as described above.

Figure 1:
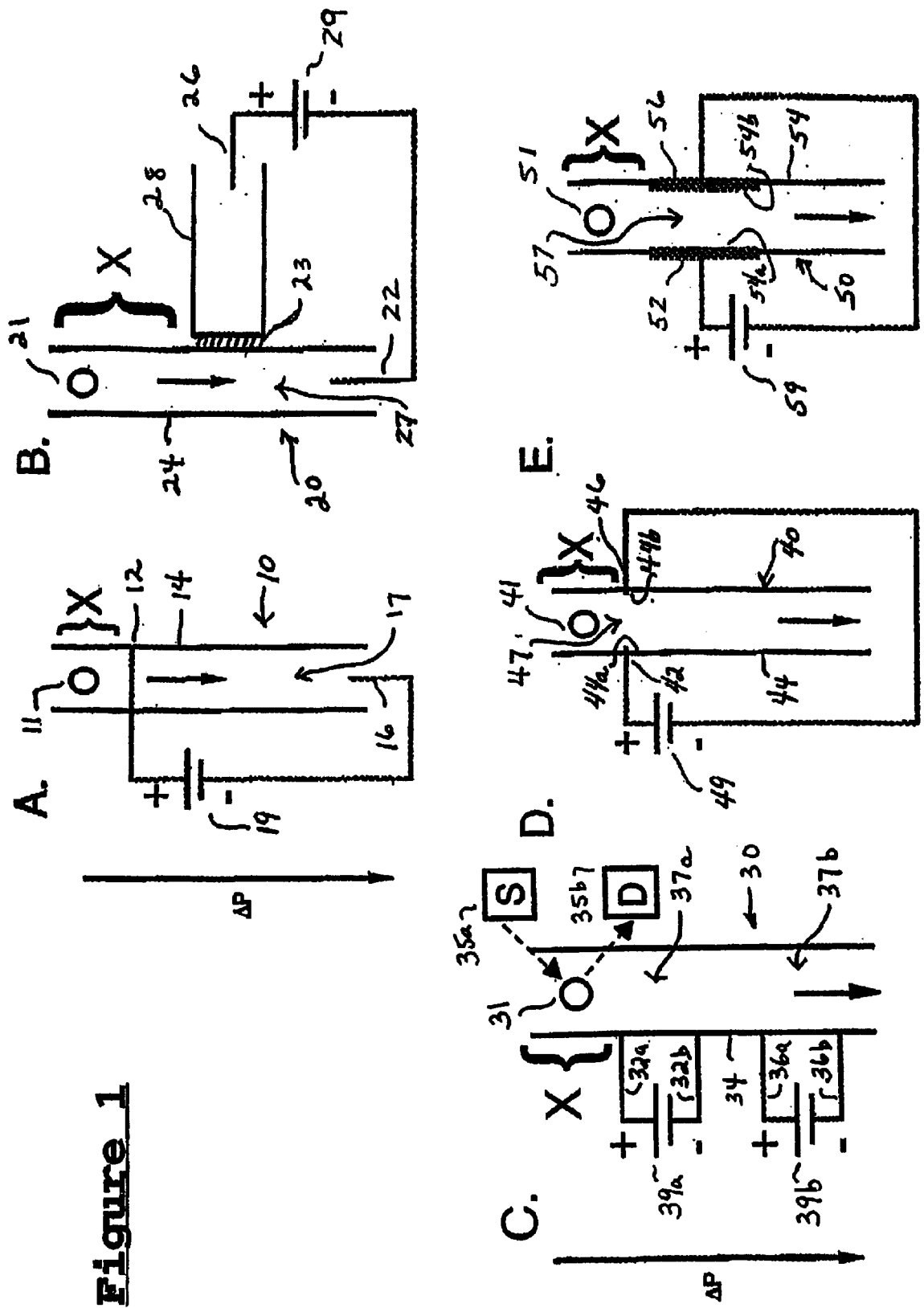
FIG. 1 includes five (5) separate diagrammatic illustrations of microchannel structures of a microfluidic system embodying the present invention.

A number of different microchannel structures on microfluidic devices embodying the present invention are diagrammatically shown in FIG. 1. The microchannel structure 10, as shown in FIG. 1A employs an electrode 12 integrated into microchannel 14, together with another electrode 16, preferably positioned at or near the end of channel 14, to apply an electric field of sufficient strength in cell lysis region 17 to lyse cell 11. The substrate of this device is advantageously fabricated out of PDMS, which allows gaseous electrolysis products generated at the integrated electrode 12 to be removed by rapid diffusion through the PDMS, as disclosed in the aforementioned U.S. patent application Ser. No. 09/244,914. In this and other embodiments that include an in-channel electrode, the electrode may be integrated, in part, on the cover plate of the device. The electric field is generated by a source of electric potential 19, which is connected to electrodes 12 and 16. The arrow in microchannel 14 indicates the direction of sample flow as a cell-containing fluid sample traverses the flow path along the microchannel.

In the microchannel structure 20 of FIG. 1B, a bridging membrane 23, as disclosed in the aforementioned U.S. patent application Ser. No. 09/244,914, may be used to provide electrical contact between channel 24 and channel 28, and thereby minimize concurrent fluid flow. Electrode 22 is preferably placed at or near the end of channel 24, e.g. in a reservoir (not shown) in fluid communication with channel 24, and electrode 26 is similarly placed in channel 28. The electrodes are connected to a source of electrical potential 29, which is operative to apply an electric field to cell lysis region 27, thus inducing lysis of cell 21. The arrow in microchannel 24 has the same significance as mentioned above, with reference to FIG. 1A.

In the microchannel structure 30 shown in FIG. 1C, microchannel 34 has four electrodes 32a, 32b, 36a, 36b. Several modes of operation are possible with this design. In a first mode of operation, electrodes 32a and 32b with an electric potential applied are used for cell lysis, and electrodes 36a and 36b are not needed. The presence of a cell 31 in zone 37a can be determined by a change in conductivity and can be used to trigger events such as the application of a cell lysis electric field in zone 37a between electrodes 32a and 32b, the recording of a time mark to indicate the start of a separation process, or fluid control actions, such as starting or stopping flow to control transport of the triggering cell or other cells. Separation and/or analysis of the contents of cell 31 may be performed in the microchannel space downstream of zone 37a. In a second mode of operation, electrodes 32a and 32b can be used for cell lysis in zone 37a, and electrodes 36a and 36b can be used for electrokinetic separations in zone 37b. This allows field strengths of different magnitudes to be used for cell lysis in zone 37a and separation in zone 37b. Also, electrodes 32b and 36a can be common for this mode of operation. A third mode of operation uses electrodes 32a and 32b to detect the presence of a cell 31 in zone 37a by a change in conductivity. This change in conductivity can be used to trigger the cell lysis electric field in zone 37b between electrodes 36a and 36b. Also, electrodes 32b and 36a can be common for this mode of operation. Electrodes 32a, 32b, 36a, 36b can be positioned at, in, or near microchannel 34 to effect the above modes of operation. The pairs of electrodes 32a and 32b and 36a and 36b are connected to sources of electric potential 39a and 39b, respectively, to generate the appropriate electric fields. These electric fields can include DC and/or AC components. Also depicted is an alternative method for determining the presence of a cell in microchannel 34 using an optical probe. A light source 35a can be directed toward microchannel 34 preferably either above (as depicted with dashed line with arrow) or in zone 37a. If a cell 31 is present, scattered light including fluorescence is detected by detector 35b (depicted by dashed line with arrow). In this way, a cell lysis electric field can be generated in zone 37a between electrodes 32a and 32b, or other events as discussed above. An optical probe or conductivity measurement to detect the presence of the cell in a microchannel can be used in conjunction with any of the lysis techniques described in this application. The solid line with arrow in microchannel 34 has the same significance as mentioned above, with reference to FIG. 1A.

FIG. 1D shows a microchannel structure 40 including microchannel 44 having a longitudinal axis with a first side wall portion 44a on one side of the axis, a second side wall portion 44b on the other side of the axis and a cell lysis region 47 defined by the microchannel space between first and second electrodes 42, 46 positioned at or near side wall portions 44a and 44b, respectively. The electrodes are connected to a source of electric potential 49, which is operative to apply an electric field to cell lysis region 47, thus inducing lysis of cell 41. The arrow shown in microchannel 44 has the same significance as mentioned above, with reference to FIG. 1A.

The microchannel structure 50 shown in FIG. 1E is quite similar to that of FIG. 1D, including microchannel 54 with first and second electrodes 52, 56 positioned at or near first and second microchannel side wall portions 54a and 54b, defining a cell lysis region 57 and a source of electric potential 59, which is connected to the electrodes to generate an electric field which effects lysis of cell 51 in the cell lysis region. The microfluidic device of FIG. 1E, in contrast to that of FIG. 1D, has electrical contacts configured to prolong the residence time of the cell(s) in the electric field. The arrow shown in microchannel 54 has the same significance as mentioned above, with reference to FIG. 1A. The embodiments of the invention described with reference to FIGS. 1A–1E can be beneficially used for analyses of cellular contents involving any number of chemical separation techniques, such as electrophoresis or chromatography.

In all of the embodiments of this invention shown in FIGS. 1A–1E, electrodes or bridging membranes can be used to make electrical contact with microchannels.

The electrode configurations in FIGS. 1D and 1E can also be used to detect the presence of a cell by measuring a change in conductivity. This change in conductivity can be used to trigger the cell lysis process. Additional electrodes configured similarly can be added to the microchannel to segregate the processes of detecting the presence of the cell and lysing the cell. Operation would be similar to that described for above FIG. 1C.

In the microchannel structures provided in the devices shown in FIGS. 1C, 1D and 1E, cell lysis can be effected by having the electrical contacts in close proximity to the microchannel, but not in physical contact with the fluid sample, and applying an AC potential.

Figure 2:
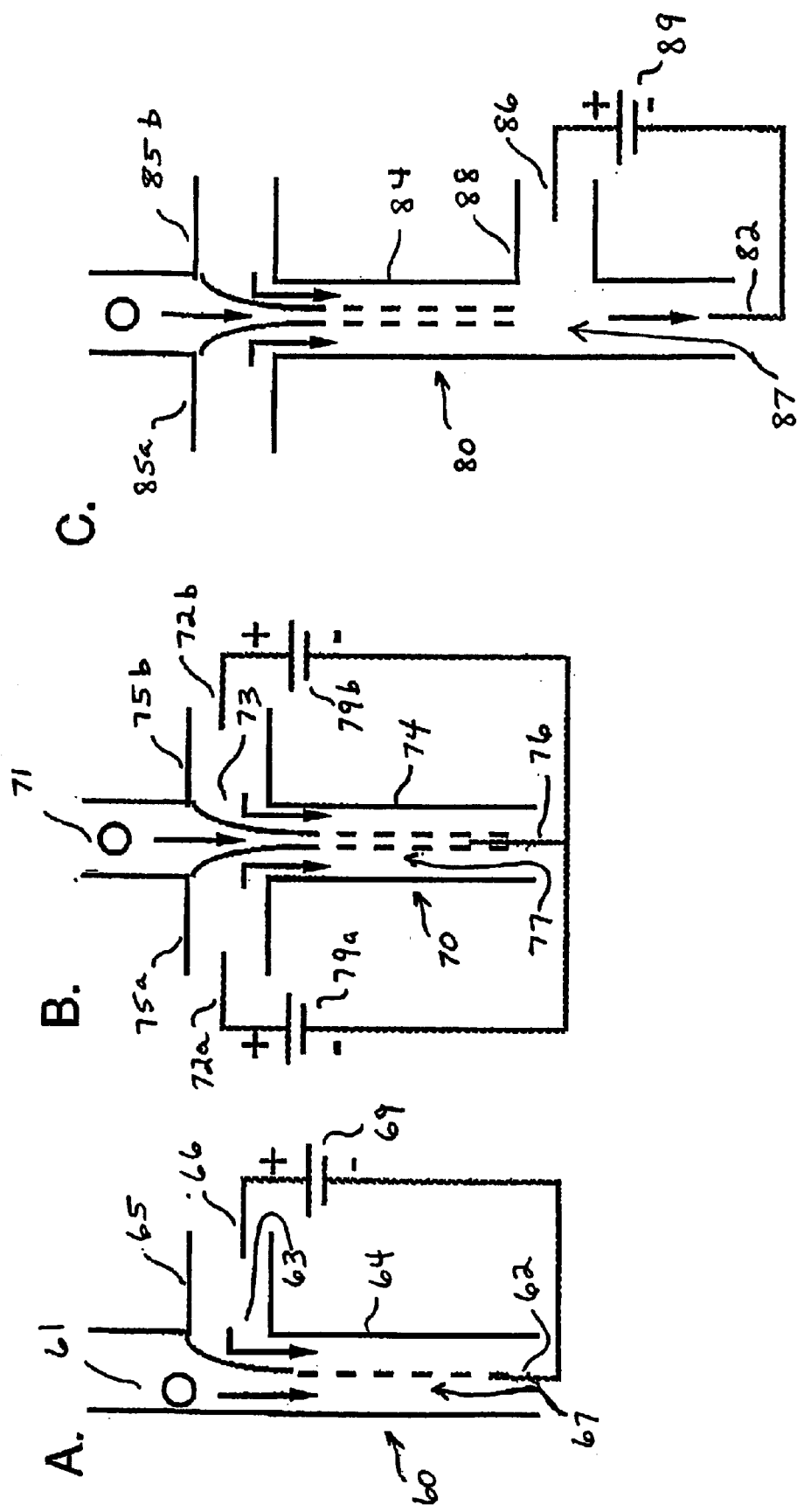
FIG. 2 includes three (3) separate diagrammatic illustrations of microchannel structures of a microfluidic system according to the present invention, including auxiliary channel segments which intersect with, and enable introduction of various agents into the microchannel, wherein cell transport and lysis occur.

In the microchannel structure 60 of FIG. 2A, microchannel 64, in which cell transport and lysis occurs, is joined by side channel 65, forming a tee-shaped intersection 63. One electrode 62 is positioned at or near the terminus of channel 64, whereas another electrode 66 is similarly positioned in microchannel 65. The electrodes are connected to a source of electrical potential 69. This electrode arrangement effectively establishes an electric field comprising the cell lysis and separation region 67 between intersection 63 and the aforementioned terminus of channel 64. Cell 61 is exposed to the electric field as it enters intersection 63.

An operational advantage of this embodiment of the invention is that a fluid can be introduced through side microchannel 65, e.g., from a reservoir (not shown) in fluid communication with side microchannel 65, to alter the buffer composition in transport/lysis microchannel 64. In this way, the conductivity of the cell-containing fluid sample may be reduced, thus diminishing the risk of Joule heating of the fluid sample, which can occur when a high electric field is applied to cell-containing samples prepared using conventional physiological buffers, e.g., phosphate buffered saline (PBS). The inclusion of an intersecting side channel also enables the addition of a chemical lysing or solubilization agent, e.g., a surfactant, to the fluid sample in transport/lysis microchannel 64. In addition, the rate of flow of material along each intersecting microchannel may be adjusted to provide various mixing ratios, either by changing the flow resistance in the channels, by altering the applied pressure or applied field strength.

The embodiment of FIG. 2B is analogous to that of FIG. 2A, in that it is in the form of a microchannel structure 70, including a transport/lysis microchannel 74 which is intersected by a side channel. In this case, however, a pair of opposed side channels 75a and 75b form a cross-intersection 73 with microchannel 74. Each side channel has an electrode 72a, 72b positioned at or near the terminus thereof, e.g., in a reservoir (not shown) containing a dilution buffer, solubilization agent, chemical lysis agent, or the like. Another electrode 76 is positioned at the lower end of microchannel 74 and is connected to two (2) separate sources of electric potential 79a, 79b, which are also connected to electrodes 72a apt and 72b, thus establishing an electric field comprising cell lysis and separation region 77, within the microchannel space between the intersection 73 and electrode 76. Cell 71 is exposed to lysis conditions upon entering cross-intersection 73. This embodiment provides all of the operational advantages of the microfluidic device shown in FIG. 2A and additionally enables cells to be exposed even more quickly and symmetrically to the effects of any chemical lysis agent or lipid membrane solubilization agent. Although two sources of electric potential, are depicted in FIG. 2B, only one source is needed to effect lysis, e.g. 79a or 79b, with electrode 72a and/or 72b connected to the single source of electrical potential.

Another approach to overcoming the high conductivity problem experienced when using cell-containing fluid samples, e.g. PBS, is illustrated in the microchannel structure 80 of FIG. 2C. This embodiment, like that of FIG. 2B, includes a microchannel 84, with a pair of opposing side channels 85a and 85b in a cross design. The function of the side channels is to introduce dilution buffer, chemical lysing agent or a solubilization agent into transport/lysis microchannel 84. One electrode 82 is positioned downstream of intersection 83, formed between side microchannels 85a, 85b and transport/lysis microchannel 84, e.g., in a waste reservoir (not shown) in fluid communication with microchannel 84. Another electrode 86 is positioned at or near the terminus of auxiliary channel 88. The electrodes are connected to a source of electric potential 89 to generate an electric field comprising cell lysis region 87 within the lower portion of microchannel 84. Using this design, a dilution buffer or other fluid can be introduced into microchannel 84 through side channels 85a, 85b or both of them, which dilutes the cell-containing fluid samples sufficiently such that a high electric field may be applied in the lower segment of microchannel 84. A microchip design having only one side channel, 85a or 85b, can achieve a similar result.

The arrows appearing in the microchannels shown in FIGS. 2A, 2B and 2C indicate the direction of flow of cells, dilution buffer or other agent, as the case may be, along the flow path within the microchannel.

It should be clear that under appropriate conditions, cells may be lysed using only a chemical lysing agent added through channel(s) 85a and/or 85b, with subsequent chemical separation, e.g. electrophoresis or chromatography, taking place in the cell lysis region, 87.

In addition to cellular analysis, it would be possible to perform other types of analyses using this type of structure. An example would be the analysis of compounds that are produced by solid phase synthesis on beads made of materials such as polystyrene. It is possible to design covalent linkers that hold the compounds on the beads such that they will be released when exposed to appropriate reagents. In this case such a chemical additive could be added at the channels 65 (FIG. 2A), 75a (FIG. 2B) or 85a, 85b (FIG. 2C) to release the bead bound compounds. Subsequent analysis by various techniques including chemical separations, flow injection analysis, or mass spectrometry after electrospray ionization could then be performed.

Figure 3:
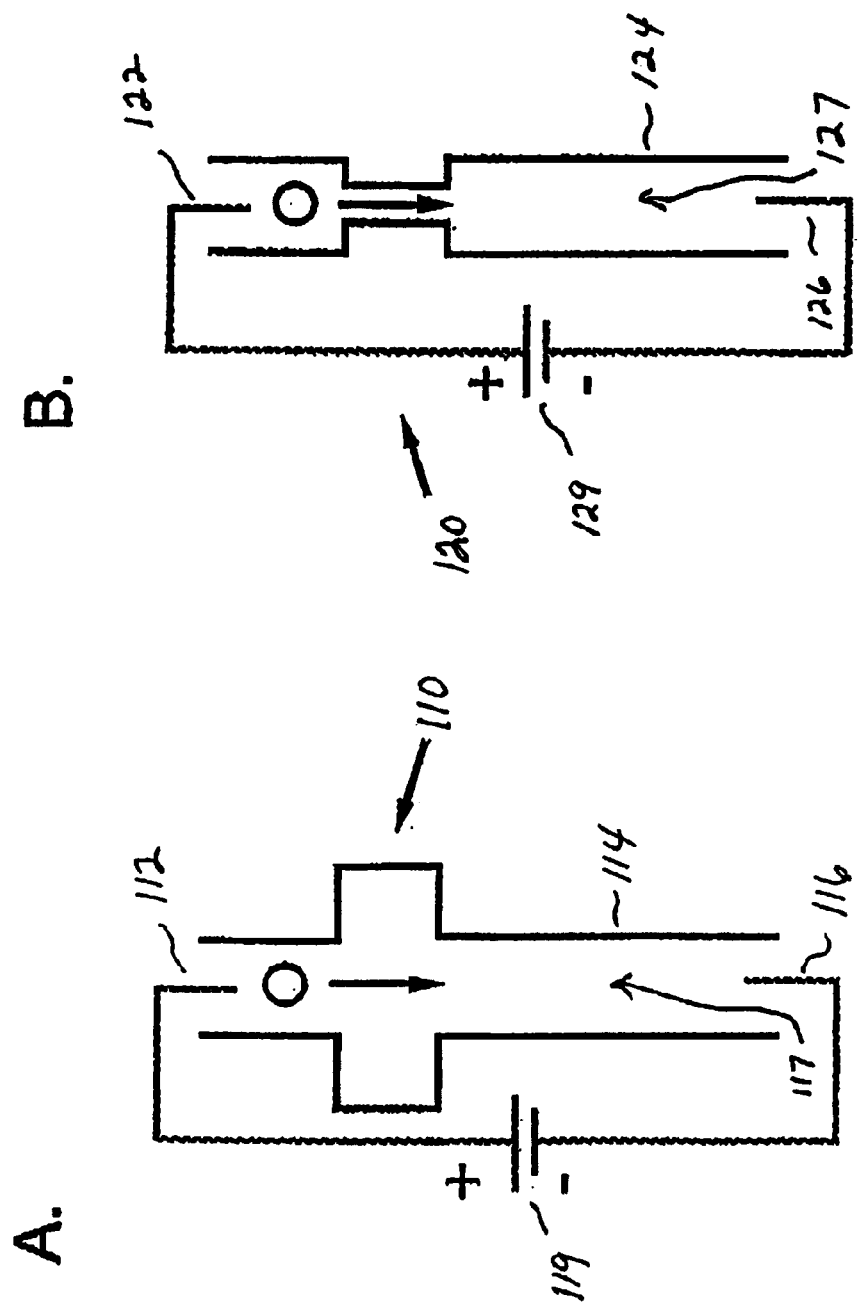
FIG. 3 provides two (2) diagrammatic illustrations of microchannel structures of a microfluidic system according to the present invention, in which a cross-section dimension of the transport/lysis microchannel is varied, either by expansion (FIG. 3A) or constriction (FIG. 3B), to change the field strength to which the cell is exposed.

FIGS. 3A and 3B illustrate microchannel structures in which a change in applied electric field strength within a microchannel is effected by varying a cross-sectional dimension of the microchannel. The embodiments shown in FIGS. 3A and 3B are similar in that each microchannel structure 110, 120 includes a pair of electrodes 112, 116 and 122, 126 positioned at spaced apart sites along microchannels 114, 124, each electrode being connected to a source of electric potential 119, 129. In this way, a cell lysis region 117, 127 is established within the electric field applied between the electrodes. In FIG. 3A, a portion of microchannel 114 is expanded relative to the remainder of the microchannel, whereas in FIG. 3B, a portion of microchannel 124 is constricted relative to the remainder of the microchannel. By abruptly increasing and then decreasing the channel width, for example, or vice-versa, the electric field strength also changes abruptly, generating sufficient force to lyse the cell.

The arrows shown in microchannels 114, 124 of FIGS. 3A and 3B, respectively, have the same significance as mentioned above, with reference to FIG. 1A.

Figure 4:
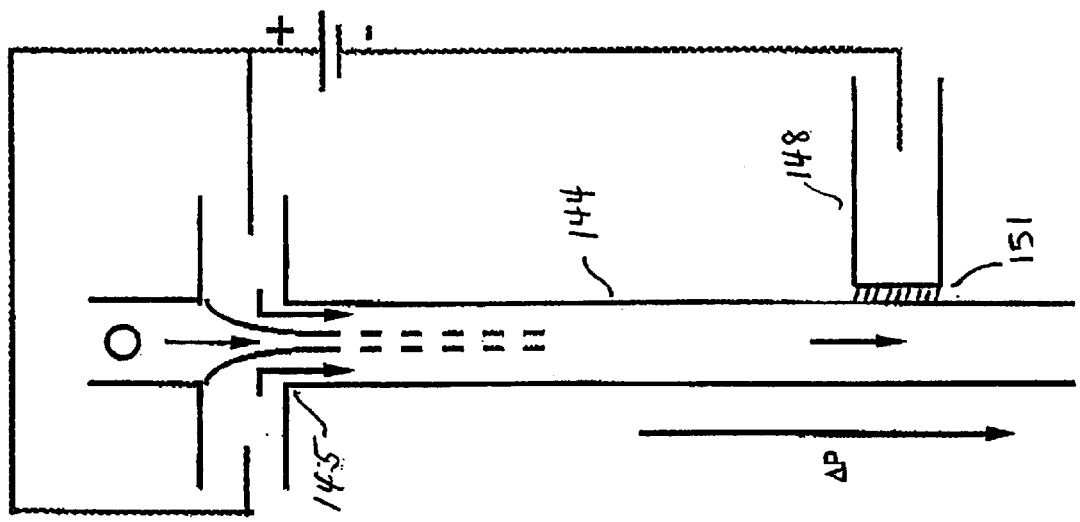
FIG. 4 includes two (2) diagrammatic illustrations of microchannel structures of a microfluidic system according to the present invention, which are designed to avoid possible interference with hydraulic pressure operating on sample fluid in the transport/lysis microchannel, due to evolution of gas at an electrode or electrodes positioned in or near the transport/lysis microchannel, e.g. in a channel or fluid reservoir where pressure is applied. This may be accomplished by placing the electrodes at the end of an auxiliary channel, as see in FIG. 4A, or in a channel connected to transport/lysis microchannel via a bridging membrane, as see in FIG. 4B.
Figure 4:
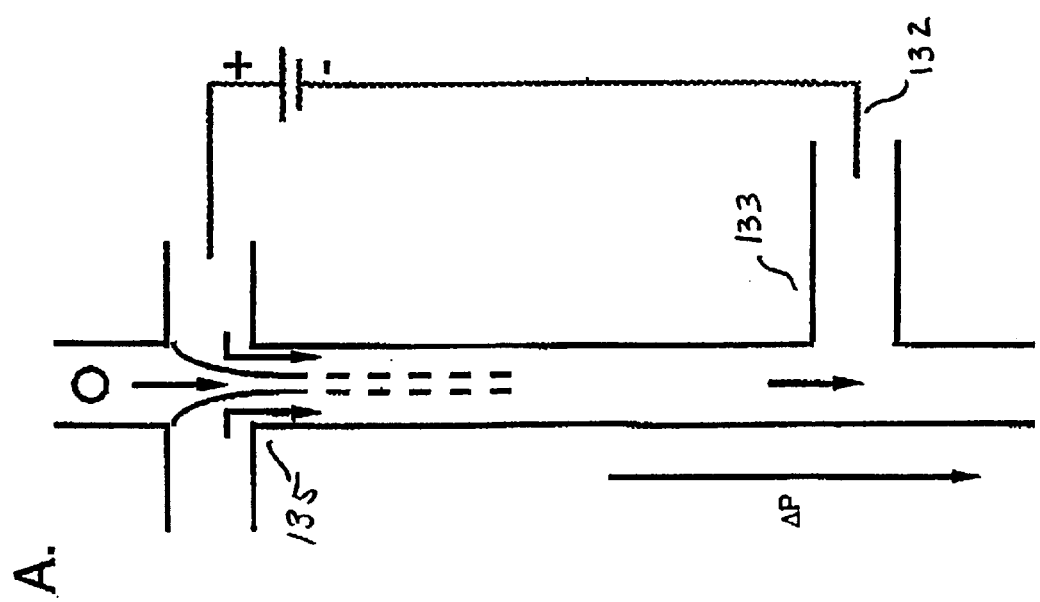

When hydraulic pressure is applied to a microchip device, as described herein, using the same reservoir or other site at which an electrode is placed, the fluid flow can be adversely affected by the evolution of gas at the electrode. This problem can be overcome by repositioning the electrode as shown in FIG. 4. For example, electrode 132 can be placed at or near the end of auxiliary microchannel 133, as shown in FIG. 4A downstream of intersection 135, or at or near the end of microchannel 148 that is connected downstream of intersection 145 to a portion of microchannel 144 via bridging membrane 151, as shown in FIG. 4B. Any gaseous electrolysis products that may be generated at the electrode can be vented to atmosphere, e.g., through a reservoir (not shown) in fluid communication with auxiliary channel 133 or channel 148, as the case may be, without interfering with the fluid flow.

Figure 5:
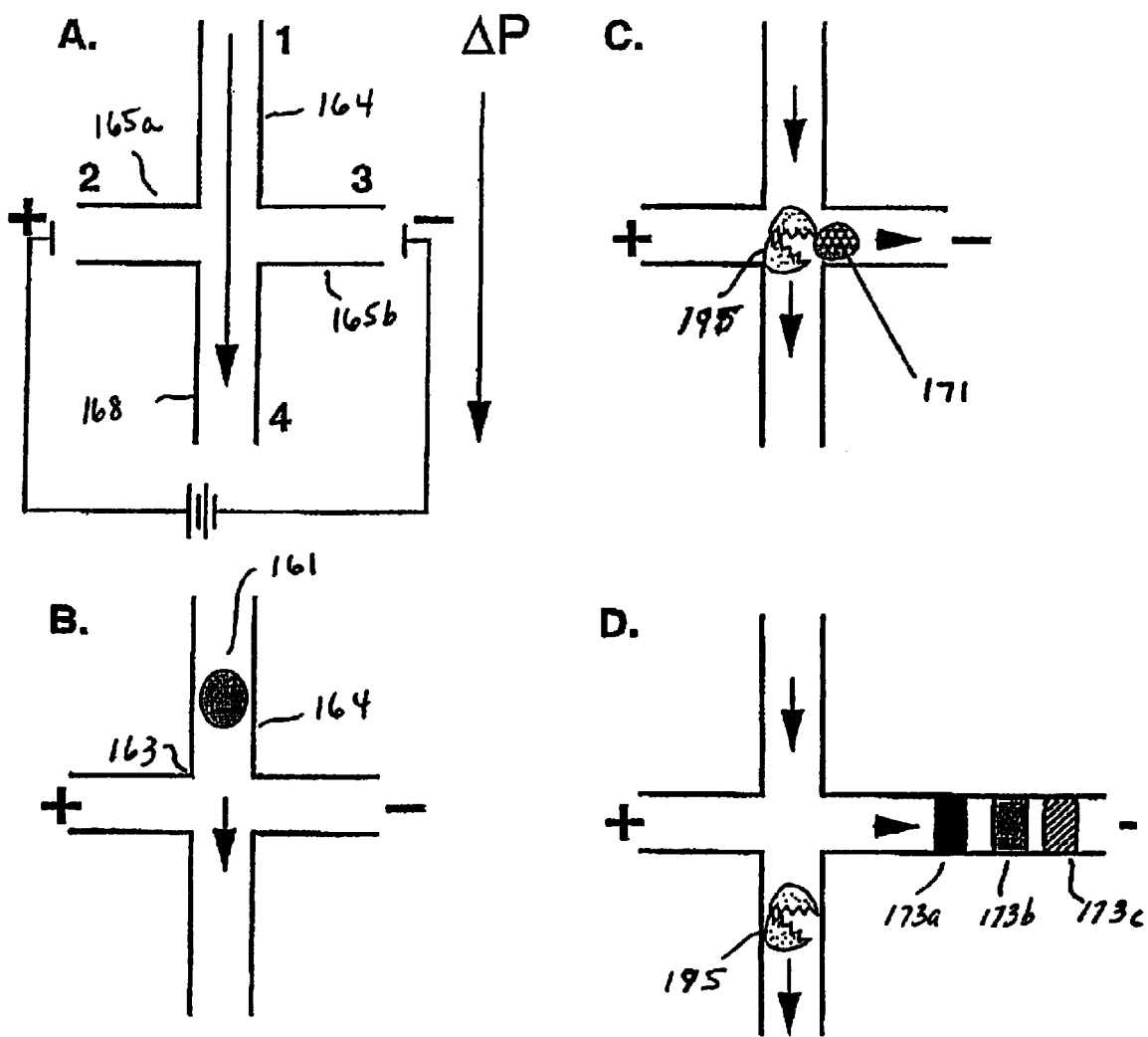
FIG. 5 is a diagrammatic illustration of cell lysis and lysate separation performed in a microfluidic system according to the present invention, having an electric field transverse to the direction of flow of the cell-containing fluid sample.

Another embodiment of a microfluidic system embodying the present invention is shown in FIG. 5. At least one cell 161 is transported through microchannel 164 by the application of hydraulic pressure to the system. The pressure can be super-ambient and applied at channel segment 164, 165a and 165b, or sub-ambient and applied at channel segment 168. In this latter case, microchannels 164, 165a, 165b must be proportioned correctly to obtain the desired flow rates in each channel. This will establish the direction of flow as indicated by the arrow in FIG. 5A. The channels can be fabricated so that most of the cell-containing sample passes from channel segment 164 to channel segment 168. The side channels 165a and 165b may be fabricated so that the resistance to hydro-dynamic flow (R) is substantially higher than that of channel segment 164. Flow resistance (R) can be controlled by adjusting the length of the channel segment and/or its cross-sectional area. The flow resistance can be made much larger for the side channels than for microchannel segment 164. An electric field is applied between channel segments 165a and 165b, as shown in FIG. 5A. This field may be DC, AC, pulsed or a combination thereof. Pressure driven flow can be used to transport the cell to intersection 163, as seen in FIG. 5B. Lysis is induced by the applied electric field and causes some of the cell lysate to form analyte plug 171 which electromigrates into one of the side channels, as seen in FIG. 5C. The analyte plug can be made to pass through microchannel segments 165a and/or 165b, depending upon whether electrosmotic flow is present and the nature of the electric charges of the species present in the cell lysate. The analyte plug can be separated into discrete segments 173a, 173b, 173c based upon chemical differences in the side channel. These analyte segments can be detected at some point downstream of the intersection.

The presence of cell 161 in the intersection 163 could be detected by a change in conductivity and can be used to trigger events such as the application of a cell lysis electric field or other procedures, as previously described.

With the appropriate pressures and voltages applied, the cellular debris 195, including the cell membrane and/or cell wall (if present), can be transported down channel segment 168 in FIG. 5D after cell lysis. This helps prevent the cellular debris from accumulating in side channels 165a and 165b and interfering with the transport of analyte plug 171. Channel segment 168 can be expanded in depth and/or width to allow greater area for the accumulation of cellular debris over time from multiple cell lysis events. Cellular debris accumulation could also be controlled using buffer additives or occasionally flushing channels 164 and 168 with a cleaning solution.

Figure 6:
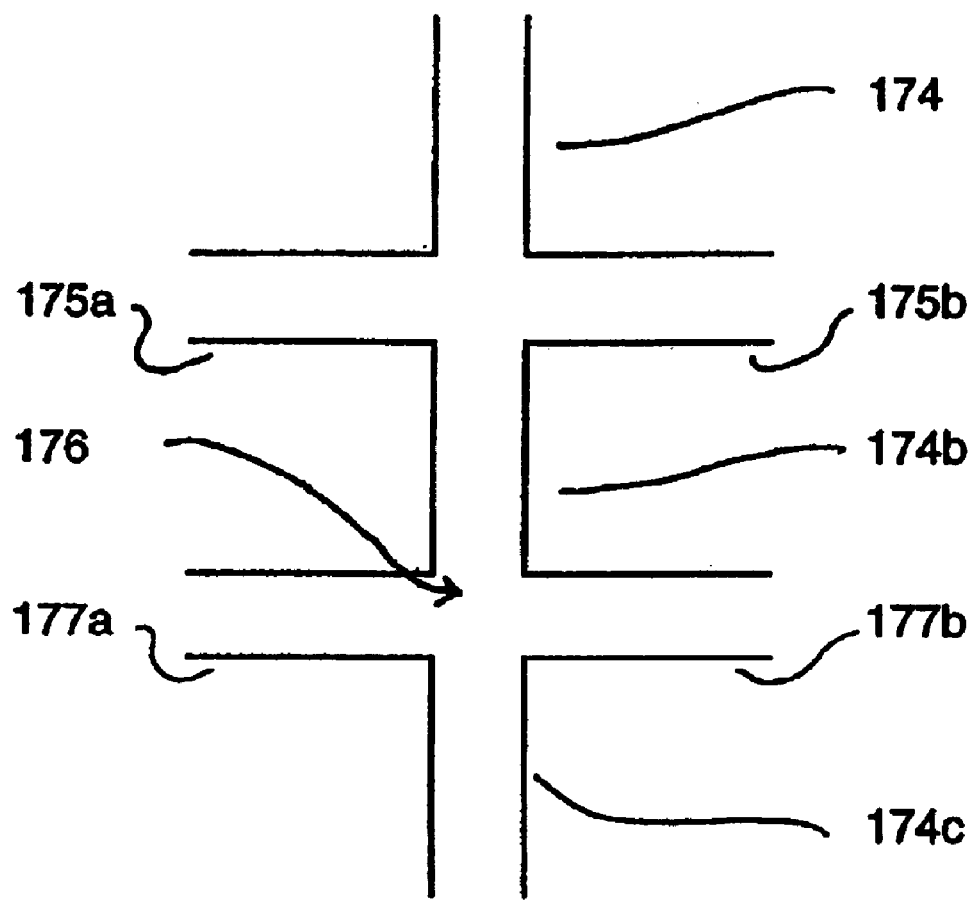
FIG. 6 is a diagrammatic illustration of a microchannel structure of a microfluidic system combining the features of flow cytometry to spatially confine and detect the presence of a cell with the feature of cell lysis, as illustrated in FIG. 5, above.

The microfluidic system shown in FIG. 6 combines features of flow cytometry to spatially confine and detect the presence of the cell as described in U.S. Pat. Nos. 5,858,187 and 6,120,666, and the cell lysis features of FIG. 5, described above. The cell-containing fluid sample is transported down microchannel 174 toward channel segment 174b. Fluid streams from side channels 175a and 175b function to position the cell, preferably in the center of channel segment 174b. In channel segment 174b, the presence of the cell can be detected by scattered light, as described above with reference to FIG. 1C. Alternatively, the presence of a cell entering channel 174b could be detected by monitoring the conductivity of the solution between channels 175a and 175b. Knowledge of a cell transiting channel 174b toward intersection 176 could be used to trigger various events such as previously described, e.g., application of the lysis electric potential, data collection, or adjusting fluid flow in various channels to control cell arrival frequency. When the cell arrives in the cell lysis region 176 at the confluence of channel segment 174b and side channels 177a and 177b, the cell is lysed by applying an electric field in side channels 177a and 177b across the cell lysis region 176 similar to the process described above for FIG. 5. A portion of the cell lysate can be transported into side channel 177a or 177b depending on the flow rate and electric potential applied. Proper adjustment of the flow velocity in the various channels could allow cellular debris to be transported down channel segment 174c. The cell lysate introduced into channel segment 177a or 177b is then analyzed. If a cell is present in channel segment 174b or in the cell lysis region 176 or the intracellular contents are being analyzed in side channels 177a or 177b, the transport of additional cells into channel segment 174b can be temporarily stopped by slowing or stopping the flow of cells in microchannel 174.

Similar to discussions above for FIGS. 2A, 2B and 2C, the microfluidic system described in FIG. 6 could also be used to analyze compounds bound to solid phase, synthesized beads. A chemical cleaving agent could be added through microchannels 175a and/or 175b. When a bead traverses from microchannel 174 to 174b, it is exposed to the chemical cleaving agent thus releasing the bound compounds into microchannel 174. A portion of the released compounds can be injected into microchannels 177a and/or 177b and analyzed by any desired chemical separation technique and/or flow injection analysis, but preferably an electromigration technique such as electrophoresis or electrochromatography.

In all of the microfluidic systems described herein, the cells upstream from the cell lysis region are preferably manipulated hydraulically and are not exposed to electric fields. This is shown in FIG. 1, for example, by the large "X", which indicates the field free channel segment through which cells are transported to the cell lysis region. Hydraulic pressure is the preferred motive force because electric fields tend to disrupt the normal metabolic state of a cell. However, under certain conditions of operation, low electric field strengths may also be used for cell transport and other manipulation with minimal disruption to normal cell processes. The pressure differential employed to create the hydraulic flow, indicated as $\Delta P$ in FIGS. 1, 4 and 5 can be generated external to the microfluidic device, using super-ambient or sub-ambient applied pressures, or on the device itself, using electrokinetically induced pressures, as described in the aforementioned U.S. Pat. Nos. 6,110,343 or 6,231,737 and U.S. patent application Ser. No. 09/244,914.

Flow cytometry like cellular manipulations of the type used in this invention are described in greater detail in the aforementioned U.S. Pat. Nos. 5,858,187 and 6,120,666, the entire disclosures of which are incorporated by reference herein.

In carrying out the method of the present invention, cells are lysed when they come into contact with the electric field in the cell lysis region, due to polarization of the cell membrane which results in rupture of the cell. The electric field can be constant or can vary with time. If the field changes with time, then the wave form can be applied continuously or pulses can be triggered, for instance by optical means, utilizing light scattering or fluorescence, for example, to detect the cells as they approach or enter the cell lysis region; or detecting a change in conductivity between two electrodes as a cell passes between them. The two electrodes used to detect changes in conductivity may be the same electrodes with which the electric field is applied to perform lysis.

The frequency, period, duty cycle and wave form type of the electric field can be varied to optimize the speed and efficiency of cell lysis. The electric field strength applied for cell lysis will ordinarily be in the range of 300–1200 V/cm. The specific electric field strength applied in a particular instance will depend upon the cell type, the presence or absence of a cell wall, the cell orientation in the electric field, and the cell membrane composition, among other factors.

Downstream of the cell lysis region, the released contents of the cell(s) may be analyzed by, for example, flow injection analysis, electrophoresis, electrochromatography, micellar electrochromatography, chromatography, hydrodynamic chromatography, or molecular sieving.

When a pulsed or AC field is used, a DC offset can be applied to the oscillating waveform to maintain an electric field in the channel downstream of the cell lysis region. This DC offset defines the average electric field in the channel segment used for separation and allows the electrokinetic separations of the cell lysate to continue during the minimum periods of the duty cycle. If the AC frequency of the applied electric field is sufficiently high, then the cell lysate will only experience the DC offset of the wave form. Such operating conditions might be optimal as the migration times of the analytes, which are used for identification, will be more consistent and easier to predict. Another method to generate an effective DC offset is to use a square wave form centered at zero with a duty cycle $\leq 0.50$, where the duty cycle is defined as the time spent at the high potential divided by the total cycle of time.

The microfluidic systems and methods of this invention may be used for the manipulation and analysis of a wide range of cells of potential scientific interest, including, without limitation, cells, yeasts, bacteria, algae and protists, whether pathogenic or not. Moreover, it may be possible to analyze synthetic particles such as liposomes, vesicles or beads.

The following examples describe the invention in further detail. These examples are provided for illustrative purposes only, and should in no way be construed as limiting the invention.

EXAMPLE I

Figure 7:
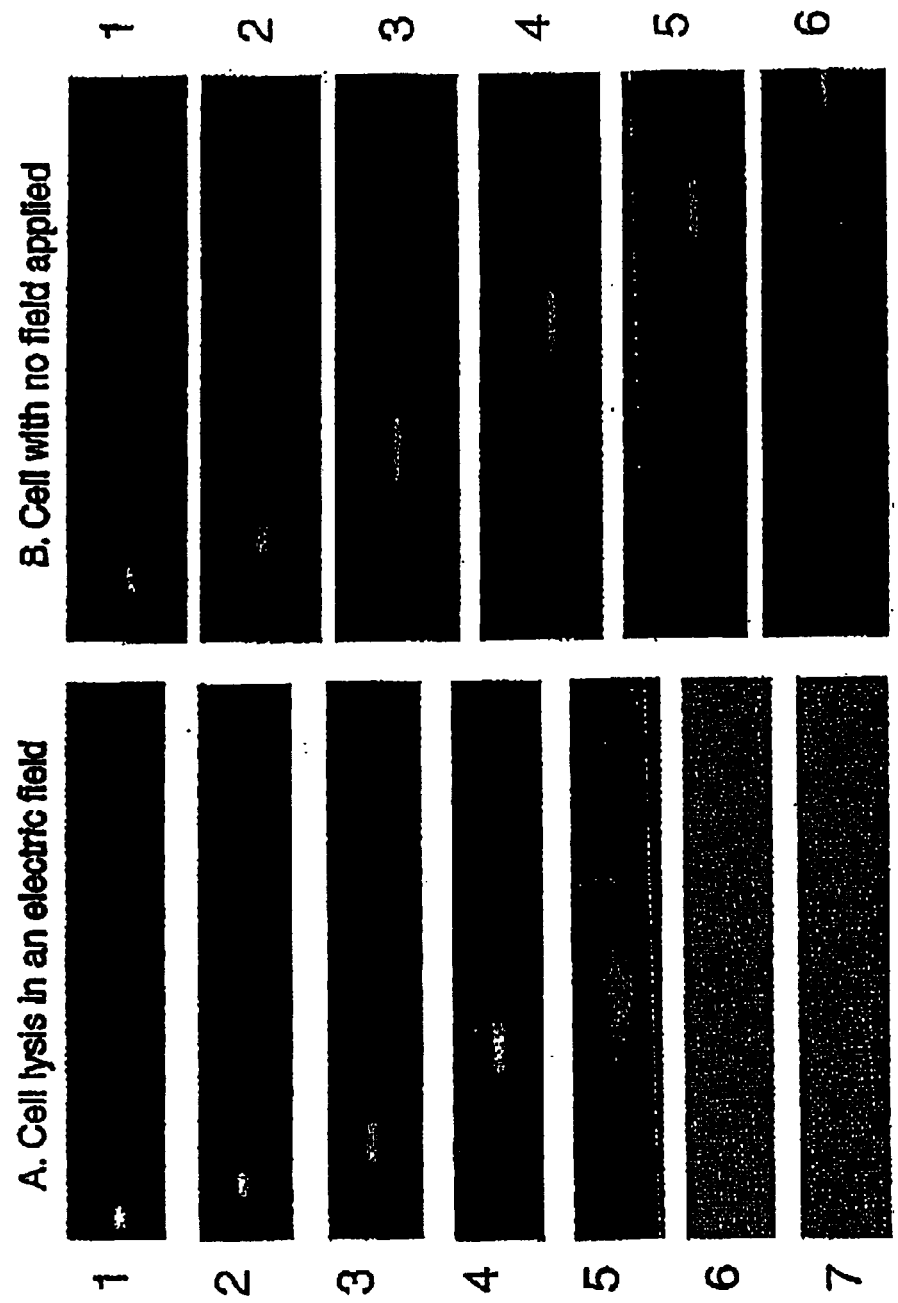
FIG. 7 includes a series of CCD camera images of cells upon exposure to an applied electric field in a microfluidic system in accordance with the present invention. Cells are lysed in a pulsed electric field, as seen in FIG. 6A (frames 1–7), but remain intact, albeit distorted, when the electric field is not applied, as seen in FIG. 6B (frames 1–6).

A microchip design of the type shown in FIG. 2B has been tested using the immortal Jurkat T lymphocyte cell line. The cells were labeled with calcein AM (Catalog #C-1430; Molecular Probes, Eugene, Oreg.) and contained in PBS. The cross intersection 73 was visualized using a video rate CCD camera (30 frames/sec) and the cells were hydraulically transported to the cross intersection by applying sub-ambient pressure to the lower segment of microchannel 74. The cells appear elongated in the images in FIG. 7 because the fluorescence signal from the calcein in the cell is integrated over 33 msec for each video frame. The streak length increases after the cell enters the lower segment of microchannel 74 because the flow rate in this channel segment is equal to the sum of the flow rates in the upper and side channel segments leading to intersection 73. A pulsed electric field (square wave) was applied between the side channel segments 75a, 75b and the lower segment of microchannel 74. At the nadir of the wave 0.35 kV was applied for 0.4 second and at the apex 2.6 kV was applied for 0.2 second. Any cell(s) present in intersection 73 or in the segment of microchannel 74 just below intersection 73 when the field was applied, were quickly lysed. Lysis was complete within about 66 msec (two video rate frames) leaving a plume of calcein in the channel (FIG. 7A, frames 4 and 5). The axial extent of the analyte plug thus obtained is small compared to the typical separation column length. Yet it is large enough that the proteolytic enzymes should be sufficiently diluted to minimize their activity. Generally, the axial length of the analyte plug will be in the range of 1 to 100 $\mu$m, but could be as large as 1 mm.

A similar experiment with only hydrodynamic flow, i.e., without an applied electric potential, is shown in FIG. 7B. The cell was not lysed during the time that it was in the field of view of the video camera (about 330 msec).

It was found that adding 25 mM sodium dodecylsulfate to side channels 75a, 75b helped to prevent the ruptured cell membrane from adhering to the channel walls downstream from intersection 73.

For the best separation results it would be advantageous to maintain a high electric field at all times during operation of the method. However, the high conductivity of the PBS sample buffer prevents a constant application of a high field because of significant Joule heating of the sample. Accordingly, a pulsed field (square wave) is recommended for use with a positive DC offset (about 350 V). The positive DC offset allows the electrokinetic separation of the cell lysate downstream of intersection 73 to continue during the low portions of the duty cycle.

EXAMPLE II

Figure 8:
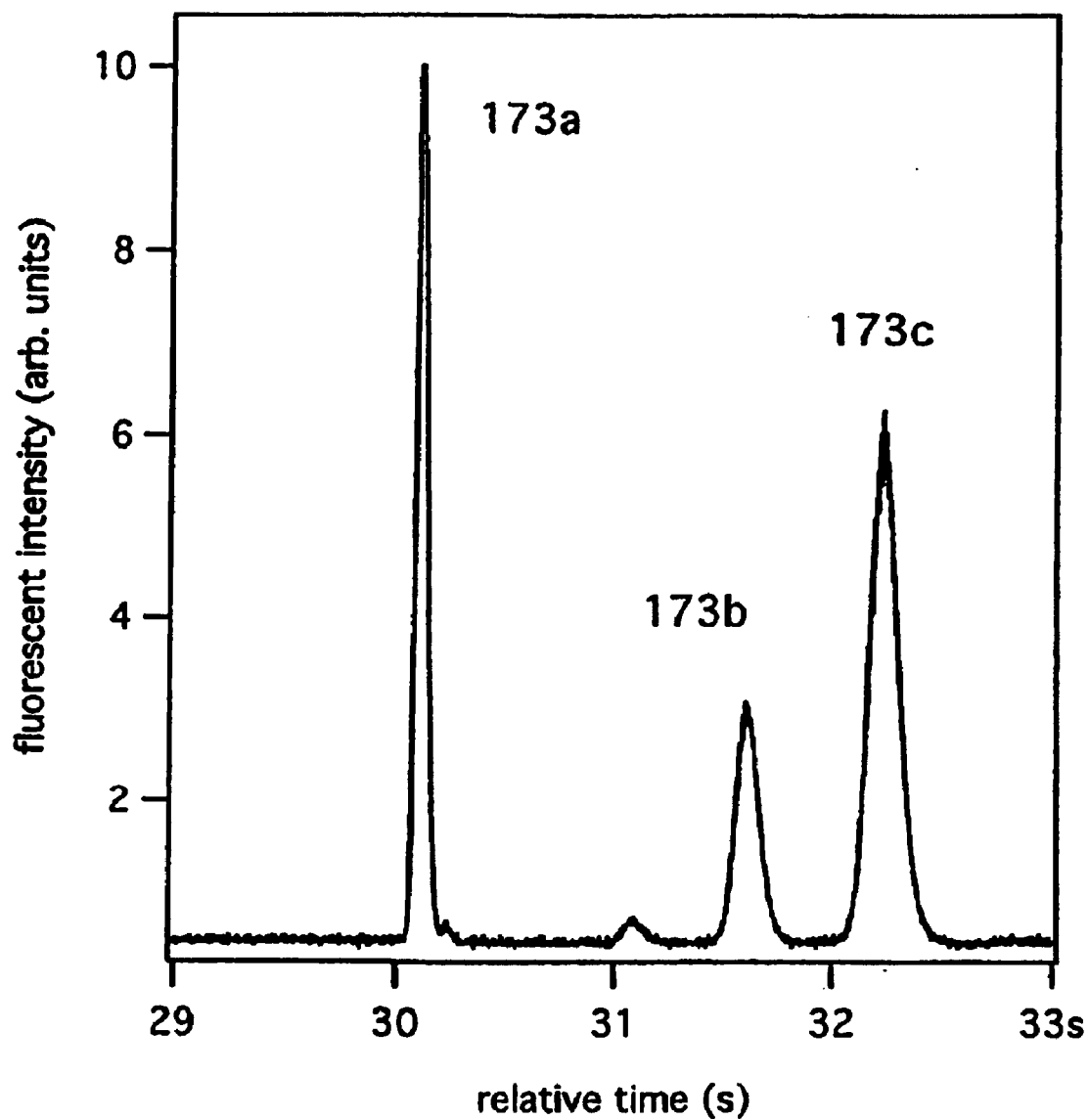
FIG. 8 is an electropherogram that depicts the analysis via electrophoresis of intracellular contents following cell lysis, in the manner illustrated in FIG. 5.

FIG. 8 shows the separation of several fluorescently labeled components released from a single cell utilizing a microchip design of the type depicted in FIG. 5, above. These components are Oregon green and some Oregon green degradation products. To generate this data, living Jurkat cells were loaded with the membrane permeable dye Oregon green diacetate. The cells 161 metabolized the dye transforming it into a membrane impermeable form that was trapped in the cell. The cell 161 was then transported through microchannel 164 to the cross intersection 163, where it was lysed by the electric field applied through channels 165a and 165b. A portion of the lysed contents in analyte plug 171 was then transported by the electric field into side channel 165b and electrophoretically separated into multiple analyte segments 173a, 173b, and 173c and detected by fluorescence.

While certain embodiments of the present invention have been described and/or exemplified above, various other embodiments will be apparent to those skilled in the art from the foregoing disclosure. The present invention is, therefore, not limited to the particular embodiments described and/or exemplified, but is capable of considerable variation and modification without departing from the scope of the appended claims.

What is claimed is:

1. A method of releasing the intracellular contents of at least one cell of a cell-containing fluid sample for analysis, said method comprising the steps of:
   a. providing a substrate having a microchannel structure which includes at least one microchannel therein;
   b. generating an electric field from a source of electric potential, said electric field being applied in a spatially defined region of said at least one microchannel, comprising a cell lysis region, and having sufficient strength to induce cell lysis;
   c. causing said cell-containing fluid sample to flow through said cell lysis region, exposing said at least one cell of said flowing fluid sample to said electric field for a time sufficient to release said intracellular contents of said at least one cell into said fluid sample, thereby providing a volume of analyte in said at least one microchannel; and analyzing said volume of analyte in said microchannel structure.

2. The method according to claim 1, including causing said cell-containing fluid sample to flow through said cell lysis region under the influence of hydraulic pressure.

3. The method according to claim 1, including causing said cell-containing fluid sample to flow through said cell lysis region under the influence of electrokinetically-induced pressure.

4. The method according to claim 1, including causing said cell-containing fluid sample to flow through said cell lysis region under the influence of an electric potential.

5. The method of claim 1 further including introduction of a chemical lysing agent into said cell lysis region.

6. The method of claim 1, wherein the strength of the electric field applied in step b. is substantially constant over time.

7. The method according to claim 6 further including the steps of detecting a change in conductivity caused by the passage of said at least one cell through said at least one microchannel, and activating said source of electric potential in response to said detected change in conductivity, thereby to produce a substantially constant electrical field.

8. The method according to claim 6, additionally including the steps of directing light at said at least one microchannel, detecting scattered light from said at least one cell in said at least one microchannel, and activating said source of electrical potential in response to said detected scattered light, thereby to produce a substantially constant electric field.

9. The method of claim 1, wherein the strength of the electric field applied in step b. varies over time.

10. The method according to claim 9 further including the steps of detecting a change in conductivity caused by the passage of said at least one cell through said at least one microchannel, and activating said source of electric potential in response to said detected change in conductivity, thereby to produce a varying electrical field.

11. The method according to claim 9, wherein said electric field applied in step b. is pulsed.

12. The method according to claim 11 further including the steps of detecting a change in conductivity caused by the passage of said at least one cell through said at least one microchannel, and activating said source of electric potential in response to said detected change in conductivity, thereby to produce a pulsed electrical field.

13. The method according to claim 12, additionally including the step of deactivating said source of electrical potential in response to a further change in said conductivity.

14. The method according to claim 9, additionally including the steps of directing light at said at least one microchannel, detecting scattered light from said at least one cell in said at least one microchannel, and activating said source of electrical potential in response to said detected scattered light, thereby to produce a varying electric field.

15. The method according to claim 11, additionally including the steps of directing light at said at least one microchannel, detecting scattered light from said at least one cell in said at least one microchannel, and activating said source of electrical potential in response to said detected scattered light, thereby to produce a pulsed electric field.

16. The method according to claim 15, additionally including the step of deactivating said source of electrical potential in response to an absence of scattered light.

17. The method of claim 1, wherein the strength of the electric field applied in step b. is caused to vary by varying at least one cross-sectional dimension of the microchannel within said cell lysis region.

18. The method according to claim 1, additionally including the step of causing said fluid sample to flow beyond said cell lysis region and performing the analysis of said volume of analyte in said microchannel structure beyond said cell lysis region.

19. The method according to claim 18, wherein said volume of analyte is analyzed by a technique selected from the group consisting of flow injection analysis, electrophoresis, chromatography, electrochromatography, micellar electrochromatography, hydrodynamic chromatography, molecular sieving, or a combination thereof, causing separation of said volume of analyte into discrete segments.

20. The method according to claim 19 further comprising subjecting at least one discrete segment to further analysis.

21. The method of claim 20, including the further step of electrospraying said at least one discrete segment for analysis by mass spectroscopy.

22. The method of claim 1, wherein said electric field is oriented axially with the direction of flow of said cell-containing fluid sample.

23. The method of claim 1, wherein said electric field is oriented perpendicularly to the direction of flow of said cell-containing fluid sample.

24. The method according to claim 1, wherein said cell-containing fluid samples flows at a pre-determined rate before and after passage through said cell lysis region.

25. The method according to claim 1, wherein the cell-containing fluid sample exposed to said electric field comprises a single cell.

26. A microfluidic system for transport and lysis of at least one cell of a cell-containing fluid sample, said system comprising a source of electric potential, a solid substrate having at least, one microchannel with a longitudinal axis and transporting means for causing flow of a cell-containing fluid sample through said at least one microchannel, said microchannel having a first wall portion on one side of said axis, a second wall portion on another side of said axis and a cell lysis region between said first and second wall portions, a first and a second electrical contact positioned adjacent said first and second wall portions of said at least one microchannel, said first and second electrical contacts being spatially separated by said cell lysis region and being electrically isolated from one another, said first and second electrical contacts being connected to said source of electrical potential which is operative to apply an electric field to said flowing cell-containing fluid sample in said cell lysis region within the microchannel space between said first and second electrical contacts.

27. The microfluidic system according to claim 26, wherein said first and second wall portions are on opposite sides of said longitudinal axis.

28. The microfluidic system according to claim 26, wherein said transporting means comprises means to apply a superambient hydraulic force through said at least one microchannel upstream of said cell lysis region.

29. The microfluidic system according to claim 26, wherein said transporting means comprises means to apply a subambient hydraulic force through said at least one microchannel downstream of said cell lysis region.

30. A microfluidic system according to claim 26, wherein said first and second electrical contacts comprise areas extending longitudinally of said at least one microchannel, said areas being substantially coextensive in length with each other and with said cell lysis region.

31. The microfluidic system according to claim 26, further comprising:
means for sensing the presence of the at least one cell in said microchannel; and
means responsive to said sensing means for triggering an operational event.

32. The microfluidic system according to claim 31, wherein the operational event is selected from the group consisting of: application of a cell lysis electric field in said cell lysis region, recordation of a time mark to indicate the start of a separation process, adjustment of fluid flow to cell arrival frequency, or a combination thereof.

33. The microfluidic system according to claim 31, wherein said sensing means comprises third and fourth electrical contacts positioned adjacent to said first and second wall portions upstream of said cell lysis region.

34. The microfluidic system according to claim 31, wherein said sensing means comprises an optical probe.

35. The microfluidic system according to claim 34 wherein said optical probe comprises:

a light source adapted for directing light into said microchannel; and a light detector adapted for detecting light scattered by a cell in said microchannel.

36. A microfluidic system for transport and lysis of at least one cell of a cell-containing fluid sample and separation of the intracellular content of said at least one cell, said system comprising a solid substrate having at least one microchannel disposed therein and means for causing flow of a cell-containing fluid sample through said at least one microchannel, said microchannel having a cell transport segment and a separation segment having first and second end portions, first and second electrical contacts adjacent said microchannel, intermediate said transport segment and said separation segment, and spatially separated from one another, the microchannel space between said electrical contacts defining a cell lysis region, said electrical contacts being connected to a source of electric potential operative to apply an electric field to said flowing cell-containing fluid sample in said cell lysis region; and means between said first and second separation segment end portions for effecting separation of said intracellular contents of said at least one cell.

37. The microfluidic system according to claim 36, wherein the cross-sectional area of at least a portion of said at least one microchannel within said cell lysis region is different from the cross-sectional area of at least a portion of the remainder of said at least one microchannel.

38. The microfluidic system according to claim 37, wherein the cross-sectional area of at least a portion of said at least one microchannel within said cell lysis region is constricted relative to said cross-sectional area of at least a portion of the remainder of said at least one microchannel.

39. The microfluidic system according to claim 37, wherein the cross-sectional area of at least a portion of said at least one microchannel within said cell lysis region is expanded relative to said cross-sectional area of at least a portion of the remainder of said at least one microchannel.

40. A method of releasing and analyzing compounds from at least one particle of a particle-containing fluid sample, comprising the steps of:

a. providing a substrate having a microchannel structure which includes a first microchannel intersecting with a second microchannel at an intersection;

b. positioning a particle of a particle-containing fluid sample in said intersection, said particle containing at least one compound;

c. introducing a chemical lysing solution into said intersection through said second microchannel, whereby said at least one compound is released into the fluid sample, thereby providing a volume of analyte in said intersection;

d. causing said fluid sample containing said analyte to flow through and beyond said intersection; and then e. analyzing said volume of analyte in said first microchannel beyond said intersection.

41. The method according to claim 40, wherein the particle is a cell.

42. The method according to claim 40, wherein the particle is a synthetic particle selected from the group consisting of liposomes, vesicles, beads, or a combination thereof.

43. The method according to claim 40, wherein the particle is a solid that has the compound chemically bonded to the surface thereof.

* * * * *